United States Patent [19]

Beckwith

[11] 4,175,325
[45] Nov. 27, 1979

[54] DENTAL ARTICULATOR

[76] Inventor: Edward K. Beckwith, 303 La Marina, Santa Barbara, Calif. 93109

[21] Appl. No.: 854,523

[22] Filed: Nov. 25, 1977

[51] Int. Cl.$^2$ .................................................. A61C 11/00
[52] U.S. Cl. ......................................... 433/60; 433/65; 433/58
[58] Field of Search ............................................ 32/32

[56] References Cited

U.S. PATENT DOCUMENTS

| | | | |
|---|---|---|---|
| 1,319,737 | 10/1919 | Wadsworth | 32/32 |
| 1,471,019 | 10/1923 | Wilson | 32/32 |
| 2,697,279 | 10/1954 | Clawson | 32/32 |
| 3,808,689 | 5/1974 | Spinella | 32/32 |

Primary Examiner—Robert Peshock
Attorney, Agent, or Firm—Harry W. Brelsford

[57] ABSTRACT

A dental articulator has a generally horizontal base, one end of which acts as the lower bow. Projecting upwardly from this base is a stem. Mounted on the top of the stem by a slip-on construction is a removable hinge support. The hinge support has a pair of spaced vertical flanges, each of which has an elongated slot inclined to the horizontal at an angle approximating the angle between the jaws that the human condyles make upon forward and rearward motion. An upper bow is hinged to the flanges by a hinge pin passing through the elongated slots. Elastic bands engage both ends of the pin and the hinge support to normally keep the pin in the lower end of each slot. The bands are resilient enough to allow the operator to pull the upper bow backwardly along the condyle angle to check the teeth for forward and backward clearances and also to allow the operator to twist the upper bow with respect to the lower bow to check for clearances upon lateral movement of the teeth.

3 Claims, 6 Drawing Figures

DENTAL ARTICULATOR

This invention relates to dental articulators and has particular reference to an articulator having a readily removable upper bow and having great freedom of motion between the upper and lower bow portions of the articulator along an angle to the horizontal that simulates the motion of the condyles of the human jaw with the socket in which they operate. The various parts of the articulator are held in engagement by elastic bands, preferably common rubber bands.

BACKGROUND OF THE INVENTION

The articulator disclosed herein is useful in all types of restoration work, but has been particularly designed for crown and bridge work. Tooth restoration work in dentistry is presently more or less divided between dentures that are removable from the mouth for cleansing and tooth restorations that are generally fixed to the teeth. These latter are known as crowns and fixed bridges.

When a dentist desires to prepare crowns or fixed bridges, he prepares the natural tooth by grinding to a suitable form to allow for sufficient bulk of metal or porcelain when the metal or porcelain is fabricated into crowns and cemented into place over the prepared natural tooth. The dentist then takes an impression of that part of the mouth in which he has been working and then an impression of the teeth opposite that part of the mouth in which he has been working. The dentist then takes a wax bite of the entire area involved. The wax bite uses a material composed of two thin pieces of flat wax of approximately fourteen gauge in thickness with a sheet of tin foil or cellophane between the sheets. This bite is placed between the occluding surfaces of the teeth, and the patient then bites down into the wax to register the relationship between the upper and the lower jaw.

These impressions of the mouth are then used as molds and are filled with a material commonly referred to as dental stone because of its extreme hardness. When the stone has set up sufficiently hard, it is removed from the molds or impressions of the mouth, and the dentist then has a more or less perfect reproduction of the various teeth of the area in which he is working, including the grounddown tooth which is to be fitted with a crown or fixed bridge. The wax bite is then placed between the teeth formed of the dental stone to obtain the registry of the upper and lower jaws with each other. This combination of upper and lower jaws with the wax bite between them is then mounted on an articulator by covering the surfaces of both upper and lower jaw and by covering the surfaces of the lower bow of the articulator and the upper bow of the articulator with plaster of paris or similar material, which sets up all the upper and lower jaw impressions in perfect registry. The wax bite is then removed, and the casts of the teeth are now ready for building the desired kind of restoration in the conventional manner.

The gold or porcelain crown is then prepared in the usual fashion (usually by the lost wax method), and when completed it is then mounted on the cast of the prepared tooth or teeth, and the dentist or technician then checks the gold or porcelain crown for a proper fit. The human jaw has various normal motions, one of which is a forward and backward movement of the jaws relative to each other. The newly prepared crown must then be checked for such movement. Also, one of the normal movements of the human jaw is lateral or sideways movement of the teeth with respect to each other, and the dentist or technician must then next check the gold or porcelain crown for a proper clearance and freedom from obstruction by this lateral movement.

SUMMARY OF THE INVENTION

The present invention provides an improved dental articulator wherein the upper bow may be readily removed from the lower bow and wherein the dentist or dental technician may readily check the backward and forward movement between the jaws and the lateral movement of the teeth. The invention also provides an inexpensive yet solid and accurate articulator which uses elastic bands to hold the various parts in assembly and to keep the upper bow from rotating into contact with the lower bow when this type of restraint is desired. I provide a horizontal base which acts as the lower bow, and projecting upwardly from this is a stem. A hinge support is removably mounted on the upper end of the stem with a slip-on construction, which in turn supports a hinged upper bow. A hinge pin passes through a bore and engages a pair of elongated slots which are disposed at a selected condyle angle to simulate the average angle of the human jaw. Elastic bands, preferably rubber bands, engage the ends of the hinge pin to hold it in the lowermost part of the elongated slot, which is the normal position for preparation of the teeth restoration. Another elastic band may be used to hold the slip-on hinge support rigidly in position on the upright stem. Still another elastic band may be used to hold the upper bow against rotating toward the teeth of the lower bow, which sometimes damages the teeth.

DESCRIPTION OF THE DRAWINGS

Various objects, advantages, and features of the invention will be apparent in the following description and claims, considered together with the accompanying drawings in which:

Referring to FIGS. 1, 2, and 3, an articulator 10 has a horizontal base portion 11, which acts as the lower bow of the articulator, and a base extension 12 on the right side thereof. Between them is formed a notch 13. Projecting upwardly from the base 11–12 is a generally upright stem 14 having a series of crosswise serrations 16 in the surface thereof, which acts as convenient places at which the stem may be cut or broken off to obtain greater or lesser dimensions between the upper and lower bow. Mounted on the top of the stem 16 is a hinge support 17, which has a socket 18 to fit over the upper end of the stem 14. Mounted on each end of the hinge support 17 are upright flanges 19, each of which has an elongated slot 21 formed therein. It will be noted that with respect to FIG. 1 particularly the slot 21 is at an angle with respect to the horizontal of about twenty degrees. This angle is the so-called condyle angle, which the human jaw makes with respect to the line of bite between the teeth of the upper and lower jaw. This condyle angle varies from individual to individual going from zero degrees to about thirty degrees, but an average of twenty degrees has proved to be effective for good restoration work.

Figure 1:
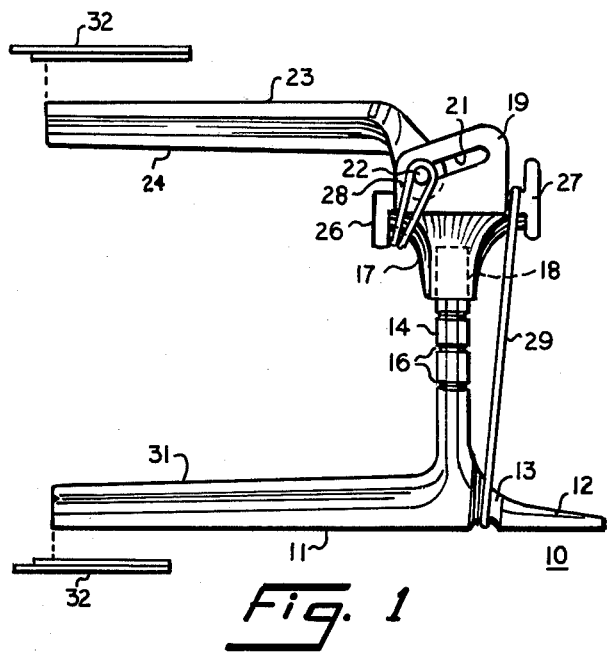
FIG. 1 is a side elevation view of an articulator embodying the invention with optional anterior plates shown in exploded position.
Figure 2:
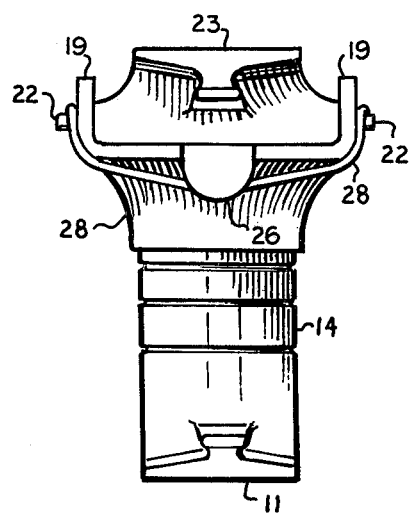
FIG. 2 is an end view of the articulator of FIG. 1 as viewed from the left end thereof.
Figure 3:
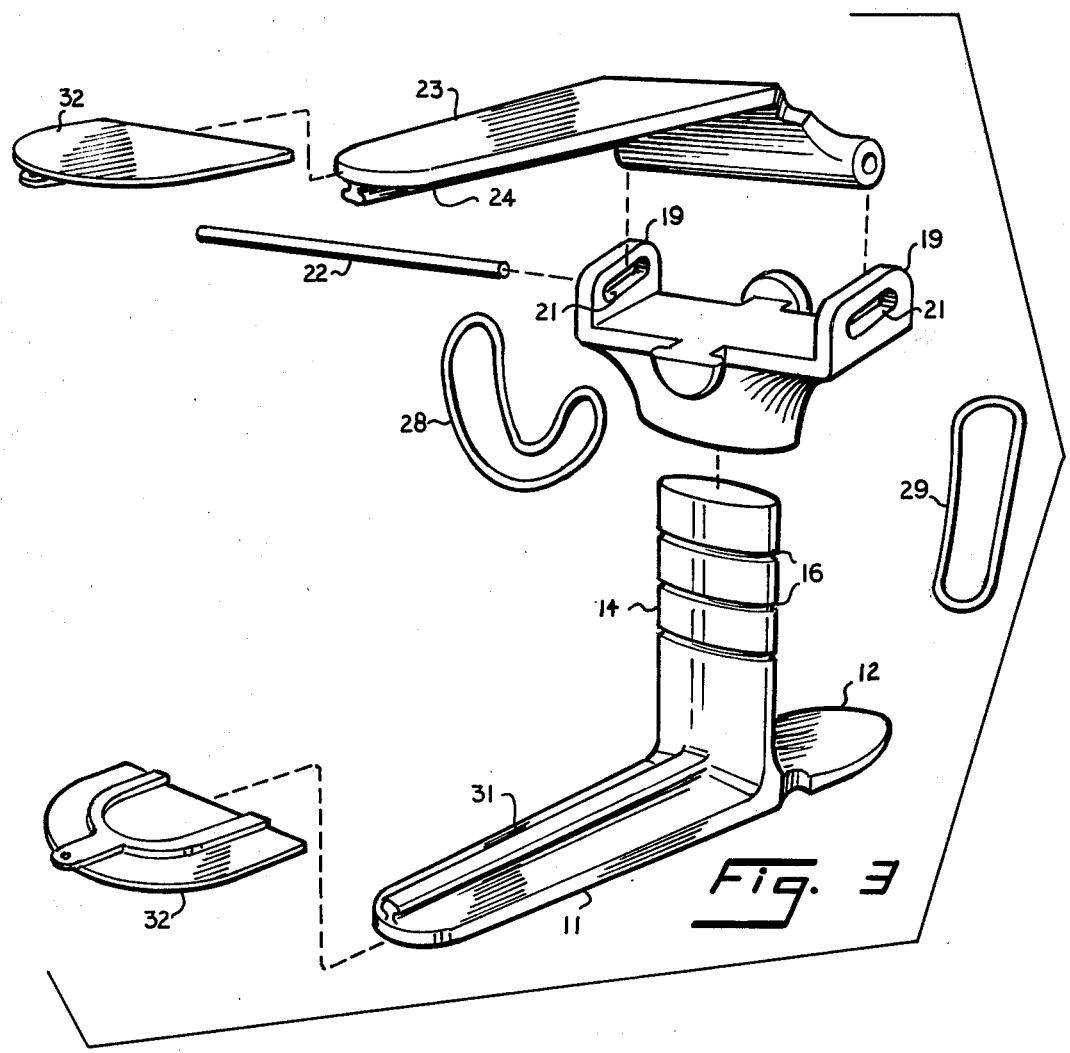
FIG. 3 is an exploded view of the articulator of FIGS. 1 and 2.

Referring still to FIGS. 1, 2, and 3, hinged to the hinge support 17 by means of a hinge pin 22 is a upper bow 23 having a generally flat top, but having a dovetail 24 secured to its underside.

Projecting from the left side of the hinge support 17 as viewed in FIG. 1 is a semicircular button 26. Secured to the right side of the hinge support 17 is a full button 27. Engaging the semicircular button 26 is an elastic tension band 28, which also engages the projecting ends of the hinge pin 22. It will be noted particularly in FIG. 1 that this elastic tension band 28 pulls the hinge pin 22 to the lowermost part of the inclined slot 21. This is the normal position of the upper bow 23 for use in making restorations with my articulator.

The hinge support 17 may be held tightly and securely to the top of the post 14 by means of a tension band 29 engaging the button 27 and the notch 13. Regarding the lower bow 11 it will be noted that this has a dovetail 31 similar to the dovetail 24 of the upper bow, and the purpose of both dovetails is to lock to each bow 23 and 11, respectively, the plaster of paris or other adhesive which will hold the cast of the teeth. When it is desired to make full-mouth impressions and casts of these impressions of the mouth, the lower bow 11 and the upper bow 23 are enlarged in size by gluing to their flat surfaces anterior plates 32, which may be extremely thin so as not to upset the steadiness of the base 11-12.

Figure 4:
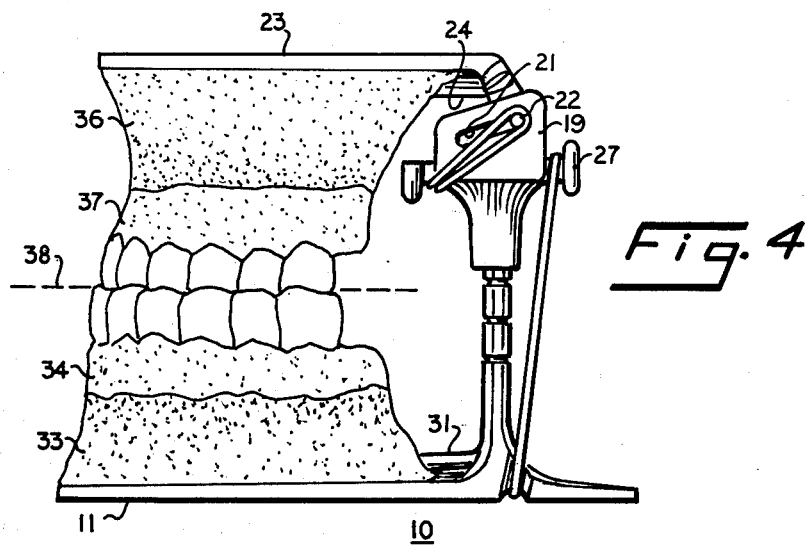
FIG. 4 is an elevation view corresponding to that of FIG. 1, but with a mold of teeth secured in place on the articulator and with the upper bow of the articulator moved rearwardly along the condyle angle with respect to the lower teeth.

Referring now to FIG. 4, it will be noted that the articulator 10 retains a cast of teeth. Accordingly, secured to the bottom bow 11 is a mass of hardened plaster of paris 33 which engages the dovetail 31 and positions a cast 34 of lower teeth. Similarly, for the upper bow 23 a mass of plaster of paris 36 is secured to its dovetail 24 and, in turn, secures and positions a cast of upper teeth 37. The average line of bite between the two sets of teeth is indicated by the line 38, which is preferably made close to horizontal, that is, parallel to the lower base 11. When this orientation of the teeth set is achieved, then the angle of the elongated slot 21 simulates the condyle angle of the human jaw joint. It will be noted in FIG. 4 that the hinge pin 22 has been manually pulled by the operator up to the upper end of the elongated slot 21. This tests the new restoration tooth for any interference with this normal back-and-forth movement of the jaw.

Figure 5:
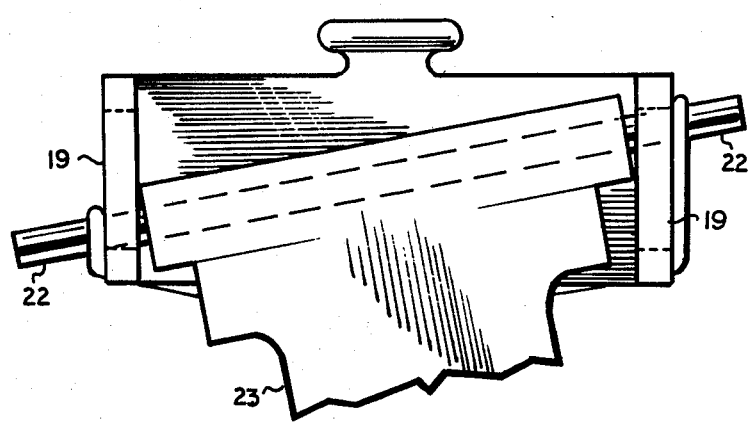
FIG. 5 is a fragmentary plan view of the articulator of FIG. 1 wherein the hinge pin has been twisted with respect to the hinge support to obtain a lateral movement in one direction of the teeth secured to the articulator.

Referring to FIG. 5, it will there be noted that the operator has twisted the hinge pin 22 in the slots in the flanges 19 so as to obtain a lateral or sideways motion of the two casts of the jaws 37 and 34 of FIG. 4. This is done manually by the operator. Again, this is done to test the clearance of the crown or bridge work with this normal movement of the human jaw.

Figure 6:
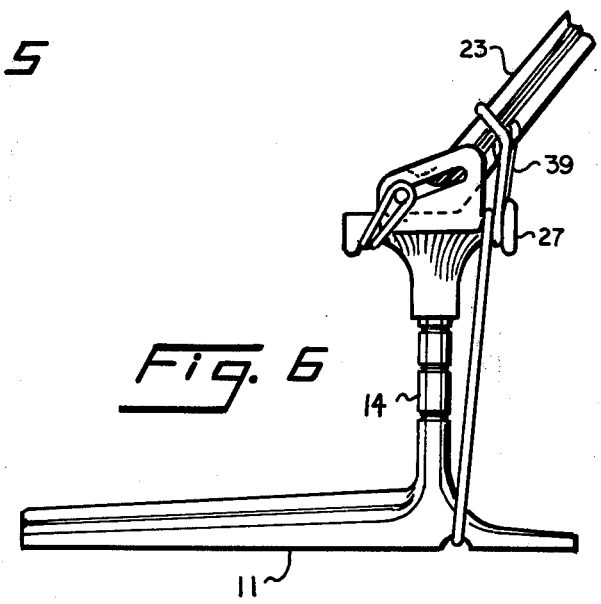
FIG. 6 is an elevation view of the articulator of FIG. 1 with part of the upper bow broken away to show the positioning of an elastic band which holds the upper bow against the rotation into contact with the lower bow.

Referring now to FIG. 6, it will be noted that an elastic tension band 39 has been passed over the upper bow 23 and around the button 27 to cause the upper bow 23 to rotate in a clockwise direction as viewed in that figure. This tension band 39 prevents any accidental slamming of the upper bow against the lower bow to thereby protect from damage any casts of teeth or porcelain or gold crowns that have been fitted on any teeth of these casts.

I prefer at present to use rubber bands for the tension bands of the disclosure, and the dentist or technician may use stronger or weaker bands as desired for his particular preference. I have designed my articulator so that it may be readily molded of plastic and therefore may be made inexpensively compared to present-day metal articulators. This permits the retention of the casts in the articulator without any great capital expenditures, and also makes the articulator highly expendable if storage space becomes a problem for the dentist or the technician. If, however, it is desired to reuse the articulator the plaster of paris is readily removed by a sharp tap from the rear of the articulator, that is, a sharp tap toward the left as viewed in FIG. 4. The dovetails 31 and 24 are slightly tapered to facilitate endwise removal of the plaster of paris from the articulator.

While I have described my invention with respect to the presently preferred embodiment thereof, as required by the statutes, I do not limit myself to this embodiment, as various modifications and variations will occur to those skilled in the art. The following claims cover all such variations and modifications that fall within the true spirit and scope of the invention.

I claim:

1. In a dental articulator having an upper and lower bow with inner and outer ends and a hinge structure joining the two inner ends, the improvement comprising:
    (a) a flat lower surface on the lower bow, which surface supports the entire articulator;
    (b) a flat upper surface on the upper bow, which surface supports the entire articulator, when it is inverted;
characterized by said bows being tapered from wide at the hinge end to narrower at the outer end so that plaster masses formed over the base may be removed by sliding them outwardly the upper surface of the lower bow and the lower surface of the upper bow have projecting dovetails that are tapered from wide at the inner end to narrow at the outer end.

2. In an articulator having an upper and lower bow hinged together, the improvement comprising:
    (a) a generally vertical stem having one end connected to one of said bows and having a noncircular cross section and formed of a material that is easily cut wherein the stem is notched so that the stem may be manually broken at the notch to shorten the stem;
    (b) a socket disposed over the other end of the stem and connected to the other bow, whereby the distance between bows may be shortened by cutting off a selected length of said other end of the stem.

3. An articulator as set forth in claim 2 wherein resilient means connect the stem and the socket to hold them in engagement.

* * * * *